US006815518B2

(12) United States Patent
Sterin

(10) Patent No.: US 6,815,518 B2
(45) Date of Patent: Nov. 9, 2004

(54) METHOD FOR PREPARING SILICONE OILS BY HYDROSILYLATION OF SYNTHONS CONTAINING AT LEAST A HYDROCARBON RING WHEREIN IS INCLUDED AN OXYGEN ATOM IN THE PRESENCE OF A CATALYTIC METAL COMPLEX

(75) Inventor: Sébastien Sterin, St-Cyr au Mont D'Or (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 10/344,651

(22) PCT Filed: Aug. 9, 2001

(86) PCT No.: PCT/FR01/02584

§ 371 (c)(1),
(2), (4) Date: Jul. 23, 2003

(87) PCT Pub. No.: WO02/14407

PCT Pub. Date: Feb. 21, 2002

(65) Prior Publication Data

US 2004/0097747 A1 May 20, 2004

(30) Foreign Application Priority Data

Aug. 17, 2000 (FR) .......................... 00 10684

(51) Int. Cl.[7] .............................................. C08G 77/08
(52) U.S. Cl. ........................................................ 528/15
(58) Field of Search ........................................... 528/15

(56) References Cited

U.S. PATENT DOCUMENTS

| | | | | |
|---|---|---|---|---|
| 5,432,140 A | * | 7/1995 | Sumpter et al. | 502/167 |
| 5,728,839 A | * | 3/1998 | Herrmann et al. | 548/103 |
| 6,124,418 A | * | 9/2000 | Crivello et al. | 528/15 |
| 6,369,265 B1 | * | 4/2002 | Nolan et al. | 560/102 |
| 6,492,525 B1 | * | 12/2002 | Bertrand et al. | 548/101 |

* cited by examiner

Primary Examiner—Margaret G. Moore

(57) ABSTRACT

The invention concerns a method for preparing functionalised silicone oils with controlled viscosity by hydrosilylation of polyorganohydrogenosiloxanes with synthons, identical or different, containing at least a hydrocarbon cycle wherein is included an oxygen atom, said reaction being carried out in the presence of a catalytic metal complex.

14 Claims, No Drawings

METHOD FOR PREPARING SILICONE OILS BY HYDROSILYLATION OF SYNTHONS CONTAINING AT LEAST A HYDROCARBON RING WHEREIN IS INCLUDED AN OXYGEN ATOM IN THE PRESENCE OF A CATALYTIC METAL COMPLEX

This application is an application under 35 U.S.C. Section 371 of International Application Number PCT/FR01/02584 filed on Aug. 09, 2001.

The present invention relates to a novel method for preparing functionalized silicone oils with controlled viscosity, containing at least one hydrocarbon ring in which is included an oxygen atom. In particular, the present invention relates to a method of hydrosilylation between polyorganohydrosiloxanes and unsaturated synthons containing at least one hydrocarbon ring in which is included an oxygen atom.

Reactions between polyorganohydrosiloxanes and olefins or acetylenic hydrocarbons are very well known. The polyorganohydrosiloxanes have, for example, the formulae:

$Me_3SiO$—$(MeHSiO)_n$—$(Me_2SiO)_m$—$SiMe_3$ in which n and m are integers or fractions such that $1 \leq n \leq 1000$ and $0 < m \leq 1000$;

$Me_2HSiO$—$(MeHSiO)_o$—$(Me_2SiO)_p$—$SiHMe_2$ in which o and p are integers or fractions such that $0 < o \leq 1000$ and $0 < p \leq 1000$.

Many synthons can functionalize polyorganohydrosiloxanes; for example, alkenes, styrenes, allyl alcohols, allyloxy ethers or allylamines are used as synthons.

These reactions are very commonly used for the synthesis of functionalized silicone oils, and the oils obtained as applications in very diverse fields such as anti-adhesion and lubrication.

In particular, functionalized oils can be prepared with 1,2-epoxy-4-vinylcyclohexane synthons. By way of application, these functionalized silicone oils are then thermally crosslinked in the presence of an acid catalyst such as hydrochloric acid or sulfuric acid, or photochemically crosslinked in the presence, for example, of a cationic photoinitiator for the preparation of anti-adhesive films for paper and/or plastics.

A very large number of catalytic compositions is used in hydrosilylation reactions. The catalytic compositions most widely known contain metals such as platinum, rhodium, cobalt or palladium. Specific examples of such catalytic compositions are platinum halides and rhodium halides, for example $H_2PtCl_6$, $PtCl_2$, $(RhCl_3 \cdot xH_2O)$, complexes of platinum with siloxanes containing unsaturated groups, complexes of platinum with olefins and cationic complexes of platinum with nitrites as ligands.

Generally, the catalytic compositions used in the hydrosilylation reaction are homogeneous catalytic compositions, i.e. said compositions are dissolved in the reaction medium. One of the compositions most widely used is the catalytic Karstedt composition described in particular in U.S. Pat. No. 3,775,452; this Karstedt composition consists of platinum complexes in which the absolute and real degree of oxidation is zero (0), and which are of formula:

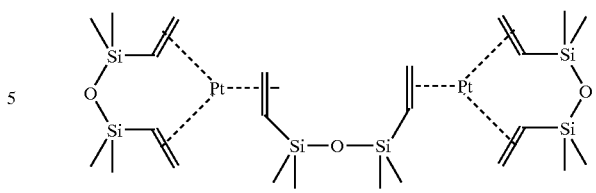

However, during the hydrosilylation reaction according to the methods of the prior art, isomerization reactions of the unsaturated synthons are observed to varying degrees, which makes it necessary to work with a molar excess of synthons relative to the polyorganohydrosiloxane in the reaction medium. This excess in the proportion of synthon causes additional expense for the industrial implementation of the method. It would therefore be desirable to reduce the required proportion of synthon, which would result in a not insignificant saving in terms of the method.

In addition, the hydrosilylation processes of the prior art are relatively unsuitable, or not at all suitable, for hydrosilylation reactions between polyorganohydrosiloxanes and synthons containing a ring in which is included an oxygen atom (epoxide, etc.). The latter, during the hydrosilylation reaction and/or the devolatilization step, have a tendency to open up and to cause uncontrolled reactions of polymerization and of crosslinking (formation of gum and/or resin) of the functionalized oils, which are initiated by the presence of the usual catalytic compositions such as the homogeneous catalytic compositions which also catalyze the polymerization of rings which include an oxygen atom.

In addition, the functionalized silicone oils obtained from usual methods are generally colored, with the order of 120 to 300 hazen, which as a result limits the domains which can be envisioned for their use, in particular in the domain of transparent and anti-adhesive films for paper or for transparent films (for example of the polyester type). This coloration is generally due to the presence in the functionalized oils of metal aggregates or of colloids of nanometric size, derived from the usual catalytic compositions. In these cases, the functionalized silicone oils require additional sets of filtration and purification in order to be usable after crosslinking in the domain of transparent films; these additional steps make industrial implementation expensive and therefore economically relatively nonviable.

The Applicant has developed a novel method for preparing functionalized silicone oils by hydrosilylation, which makes it possible to significantly reduce the isomerization reactions of the unsaturated synthon and to very substantially reduce the opening of the ring including an oxygen atom, present on the unsaturated synthon.

The method used makes it possible to obtain functionalized silicone oils which are less colored than those obtained using a method with a catalyst of the Karstedt type, which makes it possible to limit or eliminate the purification steps. Depending on the case, the oils obtained are transparent and/or translucent and can therefore be used directly in applications requiring these qualities.

In particular, the silicone oils obtained using the method of the invention can be used after crosslinking, in the domain of inks, the domain of varnishes and also in the domain of coatings, in particular films, transparent and/or anti-adhesive, through applications on supports of very varied nature; for example papers, glasses, plastics and/or metals.

According to the hydrosilylation method of the present invention, the polyorganohydrosiloxane is reacted with synthons, which may be different or identical, containing a hydrocarbon ring in which is included at least one oxygen atom. This reaction is carried out in the presence of a catalytic metal complex of formula I:

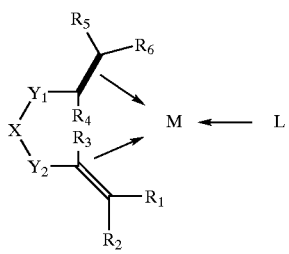

in which:

M represents a metal in the 0 oxidation state chosen from the metals of group 8 of the Periodic Table as published in Handbook of Chemistry and Physics, 65th edition, 1984–1985;

X represents O, $NR_a$ and/or $CR_fR_g$;

$Y_1$ and $Y_2$, which may be identical or different, represent $CR_bR_c$ and/or $SiR_dR_e$;

$R_1$, $R_2$, $R_5$ and $R_6$, which may be identical or different, are chosen from a hydrogen atom, an alkyl group and an aryl group optionally substituted with alkyl;

$R_3$, $R_4$, $R_a$, $R_b$, $R_c$, which may be identical or different, are chosen from a hydrogen atom; an alkyl group; an acyl group; an aryl group optionally substituted with an alkyl; a cycloalkyl group optionally substituted with an alkyl; and an arylalkyl group in which the aryl component is optionally substituted with an alkyl component;

$R_d$ and R, which may be identical or different, are chosen from an alkenyl; an alkynyl; an alkyl; an alkoxy; an acyl; an aryl optionally substituted with an alkyl; a cycloalkyl optionally substituted with an alkyl; and an arylalkyl in which the aryl component is optionally substituted with an alkyl; or else when $Y_1$ and $Y_2$, which may be identical or different, represent $SiR_dR_e$, two groups $R_d$ linked to two different silicon atoms together form:

a chain of formula:

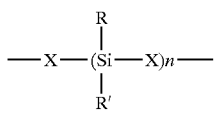

which n is an integer from 1 to 3; X is as defined above; R and R', which may be identical or different, take any one of the meanings given above for $R_e$, it being understood that, when n is 2 or 3, a single silicon atom of said chain can be substituted with one or two alkenyl or alkynyl groups;

a saturated hydrocarbon chain, the two groups $R_d$ together with said silicon atoms and X forming a 6- to 10-membered ring; or else when $Y_1$ and $Y_2$, which may be identical or different, represent $CR_bR_c$, two groups $R_b$ linked to different carbon atoms together form a saturated hydrocarbon chain, the two groups $R_b$ together with the carbon atoms which bear them and X forming a 6- to 10-membered ring;

$R_f$ and $R_g$ represent, independently of one another, a hydrogen atom; an alkyl group; an acyl group; an aryl group optionally substituted with alkyl; a cycloalkyl group optionally substituted with an alkyl; an arylalkyl group in which the aryl component is optionally substituted with alkyl; a halogen atom; an alkenyl group; an alkynyl group; or a group $SiG_1G_2G_3$ in which $G_1$, $G_2$ and $G_3$ are, independently of one another, an alkyl; an alkoxy; an aryl optionally substituted with an alkyl or an alkoxy; or an arylalkyl group in which the aryl component is optionally substituted with an alkyl or an alkoxy;

L represents a carbene of formula II:

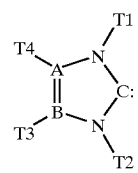

in which:

A and B, which may be identical or different, represent C or N, it being understood that, when A represents N, then $T_4$ represents nothing, and when B represents N, then $T_3$ represents nothing;

$T_3$ and $T_4$, which may be identical or different, represent a hydrogen atom; an alkyl group; a cycloalkyl group optionally substituted with an alkyl or an alkoxy; an aryl group optionally substituted with an alkyl or an alkoxy; an alkenyl group; an alkynyl group; or an arylalkyl group in which the aryl component is optionally substituted with an alkyl or an alkoxy;

$T_1$ and $T_2$, which may be identical or different, represent (i) an alkyl group; (ii) a perfluorinated alkyl group or an alkyl group optionally substituted with a perfluoroalkyl group; (iii) a cycloalkyl group optionally substituted with an alkyl or alkoxy group; (iv) an aryl group optionally substituted with an alkyl or alkoxy group; (v) an alkenyl group; (vi) an alkynyl group; or (vii) an arylalkyl group in which the aryl component is optionally substituted with an alkyl or alkoxy group;

or else $T_1$ and $T_2$, which may be identical or different, represent a monovalent radical of formula (V) below:

in which:

$V_1$ is a divalent hydrocarbon radical, preferably an optionally substituted linear or branched $C_1$–$C_{10}$ alkylene, $V_2$ is a monovalent radical chosen from the group of the following substituents:

alkoxy, $-OR^v$ with $R^v$ corresponding to hydrogen, alkyl, aryl, amine, preferably $N(R^v)_2$ with $R^v$ corresponding to hydrogen, alkyl, aryl, or else alternatively $T_1$ and $T_2$, which may be identical or different, represent a monovalent radical of formula (W) below:

in which:

$W_1$ is a divalent hydrocarbon radical, preferably an optionally substituted linear or branched $C_1$–$C_{10}$ alkylene, ω represents:
—R$^α$C=CR$^α$—, with R$^α$ corresponding to H or an alkyl group
or

—C≡C—

W$_2$ is a monovalent radical chosen from the group of the following substituents:
R$^β$=alkyl, H;
Si-alkyl or Si-alkoxy, preferably —Si(R$^δ$)$_3$ with R$^δ$=alkyl;
alcohol, preferably —C(R$^ε$)$_2$OH with R$^ε$=OH, H or alkyl;
ketone, preferably

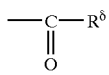

with R$^δ$=alkyl, alkenyl, alkynyl;
carboxy, preferably

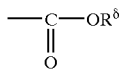

with R$^δ$=alkyl, alkenyl, alkynyl;
amide, preferably

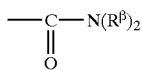

with R$^β$=H, alkyl, alkenyl, alkynyl;
acyl, preferably

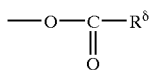

with R$^δ$=alkyl, alkenyl, alkynyl;
or else alternatively the substituents T$_1$, T$_2$, T$_3$ and T$_4$ can form, in pairs, when they are located at two adjacent points in formula II, a saturated or unsaturated hydrocarbon chain.

According to the invention, the degree of oxidation 0 of the metal M is an essential characteristic of the invention.

Preferably, M, a metal of group 8, is chosen from palladium, platinum and/or nickel. According to a more preferential embodiment of the invention, M represents platinum in the 0 oxidation state.

According to the invention, the term "alkyl" is intended to mean a saturated, linear or branched, hydrocarbon chain preferably containing from 1 to 10 carbon atoms, for example from 1 to 8 carbon atoms, better still from 1 to 7 carbon atoms. Examples of alkyl groups are in particular methyl, ethyl, isopropyl, n-propyl, tert-butyl, isobutyl, n-butyl, n-pentyl, isoamyl and 1,1-dimethylpropyl.

According to the invention, the alkyl component of the alkoxy radical is as defined above.

The perfluorinated alkyl radical or alkyl radical optionally substituted with a perfluoroalkyl group preferably has the formula: —(CH$_2$)$_p$—C$_q$F$_{2q+1}$ in which p represents 0, 1, 2, 3 or 4; q is an integer of 1 to 10; and C$_q$F$_{2q+1}$ is linear or branched. Preferred examples of this radical are:
—(CH$_2$)$_2$—(CF$_2$)$_5$—CF$_3$ and —(CF$_2$)$_7$—CF$_3$.

The expression "aryl" denotes a monocyclic or polycyclic, and preferably monocyclic or bicyclic, aromatic hydrocarbon group containing from 6 to 18 carbon atoms. It should be understood that, in the context of the invention, the expression "polycyclic aromatic radical" is intended to mean a radical having two or more aromatic rings fused to one another, i.e. having, in pairs, at least two carbons in common. By way of example, mention may be made of phenyl, naphthyl, anthryl and phenanthryl radicals.

The expression "arylalkyl" denotes an alkyl group as defined above, substituted with one or more aryl groups on its hydrocarbon chain, the aryl group being as defined above. Examples thereof are benzyl and triphenylmethyl.

According to the invention, the expression "acyl" is intended to mean a group R$_o$—CO— in which R$_o$ represents alkyl as defined above; or else a group Ar—CO— in which Ar represents an aryl group as defined above, or else arylalkyl in which aryl and alkyl are as defined above and in which the aryl component is optionally substituted with alkyl.

The expression "cycloalkyl" is intended to mean a monocyclic or polycyclic, preferably monocyclic or bicyclic, saturated hydrocarbon radical preferably containing from 3 to 10 carbon atoms, better still from 3 to 8. The expression "polycyclic saturated hydrocarbon radical" is intended to mean a radical having two or more cyclic rings attached to one another via σ bonds and/or fused in pairs. Examples of polycyclic cycloalkyl groups are adamantane and norbornane. Examples of monocyclic cycloalkyl groups are cyclopropyl, cyclobutyl, cyclopentyl, cyclohexyl, cycloheptyl and cyclooctyl.

The expression "alkenyl" is intended to mean an unsaturated, linear or branched, hydrocarbon chain exhibiting at least one olefinic double bond, and more preferably a single double bond. Preferably, the alkenyl group contains from 2 to 8 carbon atoms, better still from 2 to 6. Preferred examples of alkenyl groups are vinyl and allyl groups.

According to the invention, the expression "alkynyl" is intended to mean an unsaturated, linear or branched, hydrocarbon chain exhibiting at least one acetylenic triple bond, and more preferably a sole triple bond. Preferably, the alkynyl group contains from 2 to 8 carbon atoms, better still from 2 to 6 carbon atoms. By way of example, mention may be made of the acetylenyl group and also the propargyl group.

According to a preferred embodiment of the invention, Y$_1$ and Y$_2$ either both represent CR$_b$R$_c$, or both represent SiR$_d$R$_e$, such that the preferred compounds of the invention are either of formula I.1 or of formula I.2:

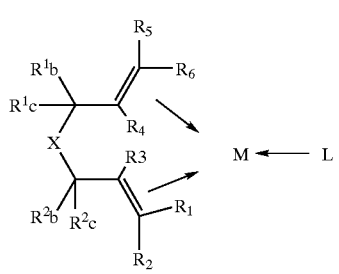

I.1

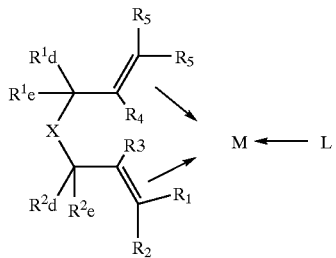

I.2

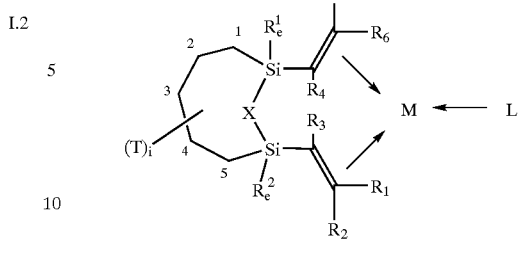

in which $R_b^1$ and $R_c^1$ are the substituents $R_b$ and $R_c$ of $Y_1$ in formula I.1;

$R_b^2$ and $R_c^2$ are the substituents $R_b$ and $R_c$ of $Y_2$ in formula I.2;

$R_d^1$ and $R_e^1$ are the substituents $R_d$ and $R_e$ of $Y_1$ in formula I.1;

and $R_d^2$ and $R_e^2$ are the substituents $R_d$ and $R_e$ of $Y_2$ in formula I.2.

Thus, $R_b^1$ may be identical to or different from $R_c^2$; $R_d^1$ may be identical to or different from $R_d^2$; and $R_e^1$ may be identical to or different from $R_e^2$.

Preferably, $R_b^1=R_b^2$; $R_c^1=R_c^2$; $R_d^1=R_d^2$; and $R_e^1=R_e^2$.

Among the latter compounds, those for which $R_3=R_4$; $R_5=R_2$; and $R_1=R_6$ are more preferred.

According to another preferred variant of the invention, $R_d^1$ and $R_d^2$ together form:

(a) either a chain

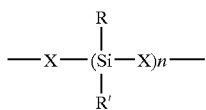

in which n is an integer from 1 to 3; X is as defined above; and R and R', which may be identical or different, take any one of the meanings given above for $R_c$, (b) or a saturated hydrocarbon chain such that the two substituents $R_d$, together with the two silicon atoms which bear them and X, form a 6- to 10-membered ring, preferably a 6- to 8-membered ring.

When $R_d^1$ and $R_d^2$ form the chain (a), it is preferred that n is equal to 1 or 2, and more particularly 1, and that $R=R_e$, the two groups $R_e$ borne by the two silicon atoms being identical. In this case, $R_e$ preferably represents alkyl, for example methyl. More particularly, in these compounds, R' represents $—CR_g=CR_1R_2$ with $R_1=R_6$, $R_2=R_5$ and $R_3=R_4$.

When $R_d^1$ and $R_d^2$ form the chain (b), it is preferred that the two groups $R_d$, together with the two silicon atoms and the group X, form an 8-membered ring. In this case, it is preferred that $R_e^1$ is identical to $R_e^2$. These compounds have the general formula:

in which T represents an alkyl group, i is an integer of between 0 and 5, T being located on one or more of the points 1, 2, 3, 4 and 5 of the formula above.

In the same way, when $Y_1$ and $Y_2$ represent $CR_bR_c$, the two groups $R_b$ bonded to different carbon atoms can together form a saturated hydrocarbon chain (c), such that the two groups $R_b$, together with the carbons which bear them and X, form a 6- to 10-membered ring. Preferably, the ring formed is an 8-membered ring, in which case the metal complex corresponds to the formula:

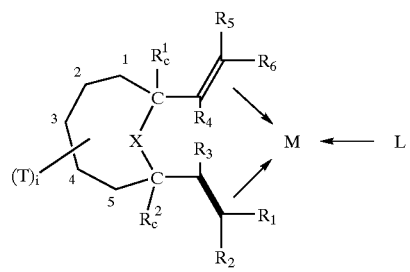

in which T represents an alkyl group; i is an integer of between 0 and 5, T being located on one or more of the points 1, 2, 3, 4 and 5 of the formula above.

In the context of the invention, two groups $R_d$ bonded to two different silicon atoms can form a chain of formula:

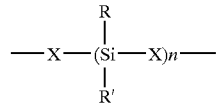

When this is the case, it is preferred that X represents O in the compounds of the invention. These preferred compounds have the general formula:

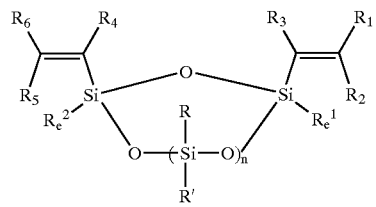

Among these compounds, it is preferred that $R_e^1=R_e^2$. Advantageously, $R_e^1=R_e^2$ represents alkyl (for example methyl).

The expression "represents nothing" means that the substituents-$T_3$, respectively-$T_4$, are nonexistent. Specifically, in the formulae II, the nitrogen atom is trivalent, such that, when A or B represents N, the nitrogen atom cannot exhibit any additional substituent.

According to a particular embodiment of the invention, the carbenes of formulae II exhibit at least two fused rings, i.e. at least two substituents from $T_1$, $T_2$, $T_3$ and $T_4$, located on two adjacent points, together form a saturated or unsaturated, hydrocarbon chain preferably containing from 3 to 6 carbon atoms. The expression "saturated or unsaturated, hydrocarbon chain" is intended to mean a linear or branched, hydrocarbon chain possibly exhibiting one or more unsaturations of the olefinic double bond or acetylenic triple bond type.

When the carbenes II exhibit two fused rings, they therefore correspond to one of the following formulae, in which (alk) represents a saturated or unsaturated, hydrocarbon chain:

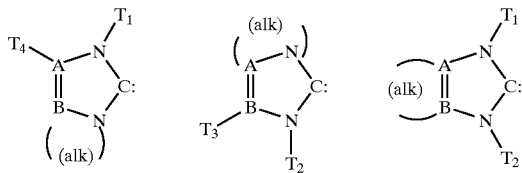

It should be understood, however, that the carbenes II can exhibit more than two fused rings.

When $R_f$ and/or $R_g$ represent $SiG_1G_2G_3$, it is preferred that $R_f$ and/or $R_g$ are trialkylsilyl, for example $SiG_1G_2G_3$ in which $G_1=G_2=G_3$=alkyl.

Subgroups of the metal complexes of the invention consist of the complexes for which:

X=O; $Y_1$ and $Y_2$ independently represent $SiR_dR_e$; or

X=$NR_a$; $Y_1$ and $Y_2$ independently represent $CR_bR_c$; or

X=$NR_a$; $Y_1$ and $Y_2$ independently represent $SiR_dR_e$; or

X=$CR_1R_g$; $Y_1$ and $Y_2$ independently represent $CR_bR_c$; or

X=$CR_fR_g$; $Y_1$ and $Y_2$ independently represent $SiR_dR_e$.

Among these 5 families of metal complexes of formula I, preference is given to those for which:

X=O; $Y_1$ and $Y_2$ independently represent $SiR_dR_e$; or

X=$NR_a$; $Y_1$ and $Y_2$ independently represent $CR_bR_c$; or

X=$CR_fR_g$; $Y_1$ and $Y_2$ independently represent $CR_bR_c$.

Very preferably, X=O and $Y_1$ and $Y_2$ independently represent $SiR_dR_e$ in the metal complex of formula I.

In the context of the invention, the expression "independently represent" means that the substituents denoted are either identical or different.

More preferably, $R_1$, $R_2$, $R_5$ and $R_6$ are hydrogen atoms.

Preferred meanings for $R_3$ and $R_4$ are in particular a hydrogen atom; an alkyl group; aryl optionally substituted with alkyl; and cycloalkyl optionally substituted with alkyl. Among these preferred meanings, it is particularly advantageous for $R_3$ and $R_4$ which are identical, to represent a hydrogen atom; $(C_3-C_8)$cycloalkyl or $(C_1-C_8)$alkyl.

More preferably, the diolefinic ligand of the complex of formula I is symmetrical, i.e. $R_5=R_2$; $R_6=R_1$; $R_3=R_4$ and the two groups $Y_1$ and $Y_2$ are either strictly identical with one another, or $Y_1=CR_b^1R_c$ and $Y_2=CR_b^2R_e$ in which $R_b^1$ and $R_b^2$ together form a symmetrical chain, or else $Y_1=SiR_d^1R_e$ and $Y_2=SiR_d^2R_e$ in which $R_d^1$ and $R_d^2$ together form a symmetrical chain.

A preferred group of complexes according to the invention consists of the complexes of formula I in which L represents a carbene of formula II. Preferably, A and B in the formulae II both represent a carbon atom.

Preferred meanings for $T_1$ and $T_2$ are alkyl; cycloalkyl; arylalkyl; and aryl optionally substituted with alkyl.

Preferred meanings for $T_3$ and $T_4$ are hydrogen; alkyl; cycloalkyl; arylalkyl; and aryl optionally substituted with alkyl.

Preferably, when $T_1$, $T_2$, $T_3$ or $T_4$ represents alkyl, then alkyl is methyl, isopropyl or tert-butyl.

Similarly, when $T_1$, $T_2$, $T_3$ or $T_4$ represents aryl, then aryl is phenyl.

When $T_1$, $T_2$, $T_3$ or $T_4$ represents aryl optionally substituted with alkyl, then $T_1$, $T_2$, $T_3$ or $T_4$ is tolyl or xylyl.

When $T_1$, $T_2$, $T_3$ or $T_4$ represents arylalkyl, then arylalkyl is preferably benzyl or triphenylmethyl.

When $T_1$, $T_2$, $T_3$ or $T_4$ represents cycloalkyl, then cycloalkyl is preferably cyclopentyl, cyclohexyl or adamantyl.

A preferred group of complexes of formula I consists of the complexes for which, in the carbene of formulae II, $T_3$ and $T_4$ represent a hydrogen atom.

Similarly, the complexes of formula I in which $T_1$ and $T_2$ are chosen from $(C_1-C_8)$alkyl and $(C_3-C_8)$cycloalkyl form a preferred subgroup. Better still, $T_1$ and $T_2$ are identical and represent $(C_3-C_8)$cycloalkyl.

Advantageously, $T_1$ and $T_2$, which may be identical or different, represent $(C_1-C_8)$alkyl or $(C_3-C_8)$cycloalkyl; or else $R_3$ and $R_4$, which may be identical or different, represent $(C_1-C_8)$alkyl or $(C_3-C_8)$cycloalkyl; or else alternatively $T_1$, $T_2$, $R_3$ and $R_4$, which may be identical or different, represent $(C_1-C_8)$alkyl or $(C_3-C_8)$cycloalkyl.

A particularly preferred group of the metal complexes of formula I consists of the complexes of formula:

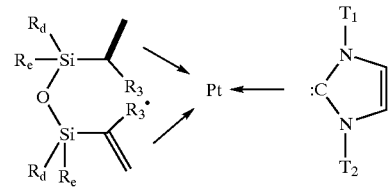

in which:

$R_3$ represents a hydrogen atom; a $(C_1-C_8)$alkyl group; or a $(C_3-C_8)$cycloalkyl group optionally substituted with $(C_1-C_4)$alkyl;

$T_1$ and $T_2$ are identical and, represent $(C_1-C_8)$alkyl or $(C_3-C_8)$cycloalkyl;

$R_d$ and $R_e$ are as defined above.

Other preferred subgroups of the invention are defined as follows:

metal complexes of formula I in which $Y_1$ and $Y_2$, which are identical, represent $SiR_dR_e$; $R_1=R_2=R_3=R_4=R_5=R_6$=H; X=O; $R_d$ and $R_e$ are independently chosen from alkyl; aryl optionally substituted with alkyl; alkenyl; and alkynyl;

metal complexes of formula I in which $Y_1$ and $Y_2$, which are identical, represent $SiR_dR_e$; X=O; $R_1=R_6$; $R_2=R_5$; $R_3=R_4$; $R_1$ and $R_2$ independently represent alkyl; $R_3$ represents alkyl or aryl optionally substituted with alkyl; $R_d$ and $R_e$ independently represent alkyl; alkenyl; alkynyl; or aryl optionally substituted with alkyl;

metal complexes of formula I in which $Y_1$ and $Y_2$, which are identical, represent $SiR_dR_e$; X=O; $R_1=R_2=R_3=R_4=R_5=R_6$=H; and $R_d=R_e$=methyl or else $R_d$=methyl and $R_e$=phenyl;

metal complexes of formula I in which $Y_1$ and $Y_2$, which are identical, represent $SiR_dR_e$; X=O; $R_1=R_3=R_4=R_6$=H; $R_2=R_5$=alkyl;

metal complexes of formula I in which $Y_1$ and $Y_2$, which are identical, represent $SiR_dR_e$; $X=CR_fR_g$; $R_f=R_g=$a hydrogen atom; $R_d$ and $R_e$, which may be identical or different, are chosen from alkyl; and aryl optionally substituted with alkyl; $R_1=R_6$; $R_2=R_5$; $R_3=R_4$; $R_1$ and $R_2$ are chosen from a hydrogen atom and an alkyl group; $R_3$ represents a hydrogen atom, alkyl or aryl optionally substituted with alkyl;

metal complexes of formula I in which $Y_1$ and $Y_2$, which are identical, represent $SiR_dR_e$; $X=CR_fR_g$ in which $R_f$ and $R_g$ represent a halogen atom, preferably a chlorine atom or a bromine atom; $R_d=R_e=$alkyl, preferably methyl; $R_1=R_2=R_3=R_4=R_5=R_6=H$;

metal complexes of formula I in which $Y_1$ and $Y_2$, which are identical, represent $SiR_dR_e$; $X=CR_fR_g$ in which $R_f$ and $R_g$ represent $SiG_1G_2G_3$ such as trialkylsilyl (for example $Si(CH_3)_3$); $R_d=R_e=$alkyl, preferably methyl; $R_1=R_2=R_3=R_4=R_5=R_6=H$;

metal complexes of formula I in which X represents $-NR_a$; $Y_1$ and $Y_2$, which are identical, represent $SiR_dR_e$; $R_1=R_6$; $R_2=R_5$; $R_3=R_4$;

metal complexes of formula I in which X represents $NR_a$; $Y_1=Y_2=SiR_dR_e$; the two groups $R_d$ together form the chain $-NR_a-(SiR_eR_d^o-NR_a)_n-$ in which $R_d^o$ represents $-CR_3=CR_1R_2$; n represents from 1 to 3; $R_1=R_6$; $R_2=R_5$; and $R_3=R_4$.

The complexes of the invention are prepared conventionally, for example from known complexes of the state of the art, by ligand exchange, i.e. by addition of the appropriate carbene of the formula II to a metal complex of the metal M, in solution, denoted precursor complex.

Suitable precursor complexes are the Karstedt complex of formula:

$Pt_2[ViMe_2Si-O-SiMe_2Vi]_3$ in which Vi represents the vinyl radical; and more generally $M_2[R_5R_6C=CR_4-Y_1-X-Y_2-CR_3=CR_1R_2]_3$ in which M, $R_5$, $R_6$, $R_4$, $R_3$, $R_1$, $R_2$, $Y_1$, X and $Y_2$ are as defined previously, such as for example:

$M_2[CR_5R_6=CR_4SiR_dR_e-O-SiR_dR_e-CR_3=CR_1R_2]_3$, it being understood that M, $R_1$, $R_2$, $R_3$, $R_4$, $R_5$, $R_6$, $R_d$ and $R_e$ are as defined above;

$Pt(COD)_2$ in which COD represents cyclooctadiene, and more generally $M(COD)_2$ in which M is a metal from group 8; or else metal complexes of olefin and bisphosphine.

The complexes of formula I are generally prepared from precursor complexes having, as ligand, at least one diolefinic compound of formula III:

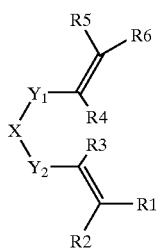

III in which $R_1$, $R_2$, $R_3$, $R_4$, $R_5$, $R_6$, X, $Y_1$ and $Y_2$ are as defined above for formula I.

These ligands are either commercially available or are easily prepared by those skilled in the art from commercial compounds.

When X represents $NR_4$ and $Y_1$ and $Y_2$, independently of one another, represent $CR_bR_c$, the compounds of formula III are commercially available amines or amines prepared in a manner known in itself from commercially available compounds.

When X represents O and Y represents $CR_bR_c$, the compounds of formula III are ethers. These ethers are commercially available or are prepared in a manner known in itself from commercially available compounds.

The compounds of formula III in which X represents $CR_fR_g$ and Y represents $CR_bR_c$ are diolefins which are readily accessible to those skilled in the art by synthesis or which are commercially available.

The compounds of formula III in which X represents $NR_a$ in which $R_a$ represents H or alkyl; $R_1=R_6$; $R_2=R_5$; $R_3=R_4$; and $Y_1=Y_2=SiR_dR_e$ can be prepared by the action of an amine $R_a-NH_2$ with two equivalents of a silyl chloride of formula: $ClSiR_dR_e-CR_3=CR_1R_2$ in which $R_e$, $R_d$, $R_1$, $R_2$ and $R_3$ are as defined above.

The compounds of formula III in which X represents $NR_a$, $R_a$ being as defined above in formula I; $Y_1=Y_2=SiR_dR_e$ in which $R_e$ is as defined above in formula I; the two groups $R_d$ together form the chain: $-NR_a-(SiR_eR_d^o-NR_a)_n-$ in which $R_a$ and $R_e$ are as defined above; n represents an integer from 1 to 3; $R_d^o$ represents $-CR_3=CR_1R_2$; $R_1=R_6$; $R_2=R_5$ and $R_3=R_4$, can be prepared by reaction of the amine $R_a-NH_2$ with the silyl chloride of formula: $Cl_2SiR_e-CR_3=CR_1R_2$ in which $R_e$, $R_1$, $R_2$ and $R_3$ are as defined above.

The compounds of formula III in which X represents O, and $Y_1$ and $Y_2$ represent $SiR_dR_e$ are linear, branched or cyclic siloxanes which are commercially available or the preparation of which is possible from commercial compounds, using the conventional methods of the state of the art. Examples of preferred siloxanes of formula III are $ViMe_2SiOSiMe_2Vi$ and $(MeViSiO)_3$, the second formula representing a cyclosiloxane in which Vi represents vinyl.

In the case of the symmetrical compounds of formula III, i.e. those for which $R_1=R_6$; $R_2=R_5$; $R_3=R_4$ and $Y_1=Y_2$, one of the following synthesis variants may be implemented.

(Variant a): To prepare said symmetrical siloxanes of formula III for which $R_1$, $R_2$, $R_3$, $R_d$ and $R_e$ are independently chosen from alkyl, aryl, alkenyl and alkynyl, a silyl chloride of formula $Cl_2SiR_dR_e$ can be reacted with an organometallic compound of formula: $CR_1R_2=CR_3-Mg-Hal$ in which $R_1$, $R_2$ and $R_3$ are as defined above and hal represents a halogen atom, under the usual conditions for reaction involving magnesium compounds.

(Variant b): To prepare said symmetrical siloxanes of formula III in which $R_1=R_2=R_3=H$, and $R_c$ and $R_d$ are chosen from alkenyl, alkynyl, aryl and alkyl, a silyl chloride of formula $Cl_2SiR_d-CH=CH_2$ can be reacted with an organometallic compound of formula: $R_e-Mg$-hal in which $R_e$ is as defined above and hal represents halogen.

To implement this variant, those skilled in the art may refer to J. Gen. Chem., USSR, 1977, 47, 1402–1406.

(Variant c): To prepare said symmetrical siloxanes of formula III in which $R_1=R_3=H$ and $R_2$ represents alkyl, a siloxane of formula: $H-SiR_dR_a-O-SiR_dR_aH$ can be reacted with two equivalents of an acetylenic hydrocarbon of formula $H-C\equiv C-R_2$ in which $R_2$ is as defined above.

Cyclic siloxanes of formula III are described in U.S. Pat. No. 4,593,084.

The compounds of formula III in which X represents $CR_fR_g$ and $Y_1$ and $Y_2$ independently represent $-SiR_dR_e$ can be prepared using a method similar to one of those described in:

J. of Organometallic Chemistry, 1996, vol. 521, 99–107 (which method is more particularly suitable for preparing the symmetrical compounds of formula III in which $Y_1=Y_2$; $R_f=R_g=H$; $R_d$ and $R_e$ represent alkyl or aryl optionally substituted with alkyl; $R_3$ represents a hydrogen atom; alkyl; or aryl optionally substituted; and $R_1$ and $R_2$ are chosen from a hydrogen atom and alkyl);

J. of Organometallic Chemistry, 1997, vol. 545–546, 185–189 (which method is more particularly suitable for preparing symmetrical compounds of formula III in which $Y_1=Y_2$; $R_f=R_g=Cl$ or Br; $R_d$ and $R_e$ represent alkyl; $R_1=R_2=R_3=$a hydrogen atom);

J. Chem. Soc., Perkin Trans II, 1987, p. 381 (which method is more particularly suitable for preparing the symmetrical compounds of formula III in which $Y_1=Y_2$; $R_f=R_g=SiG_1G_2G_3$; $R_d$ and $R_e$ represent alkyl; $R_1=R_2=R_3=$a hydrogen atom).

The carbenes of formula II can be prepared by deprotonation of imidazolium salts, of tetrazolium salts, of triazolium salts, or of pyrazolium salts, as appropriate, under the action of a base.

These reactions can be represented schematically as follows:

$$\begin{bmatrix} T_4\diagdown A \diagup N \diagdown \\ \phantom{T_4}\phantom{A}C_{(+)} \\ T_3\diagup B \diagdown N \diagup \end{bmatrix} X^- \xrightarrow{\text{base}} \begin{array}{c} T_4\diagdown A \diagup N^{T_1} \\ \phantom{T_4}\|\phantom{A}\diagdown C: \\ T_3\diagup B \diagdown N \diagup \\ \phantom{T_3}\phantom{B}\phantom{N}T_2 \end{array}$$

VIII.1        II.1

In these reaction schemes, $T_1$, $T_2$, $T_3$, $T_4$, A and B are as defined above for formula I and $X^-$ represents an anion.

The nature of the anion $X^-$ is not critical according to the invention. The anion $X^-$ is the anion derived from an organic or inorganic Brönsted acid (protic acid). Conventionally, the anion $X^-$ is derived from an acid having a pKa of less than 6. Preferably, $X^-$ is derived from an acid with a pKa of less than 4, better still less than 2. The pKas to which reference is made here are the pKas of the acids as measured in water.

Examples of acids are the carboxylic acids of formula $G_o$—COOH in which $G_o$ represents alkyl, and for example $(C_1-C_{22})$alkyl; or else aryl, and for example $(C_8-C_{18})$aryl optionally substituted with one or more alkyl(s), preferably one or more $(C_1-C_6)$alkyl(s); the sulfonic acids of formula $G_o$—SO$_3$H in which $G_o$ is as defined above; and the phosphonic acids of formula $G_o$—PO$_3$H in which $G_o$ is as defined above; other acids are HF, HCl, HBr, Hl, H$_2$SO$_4$, H$_3$PO$_4$ and HClO$_4$.

Preferred examples of carboxylic acids are acetic acid, benzoic acid and stearic acid. As a preferred sulfonic acid, mention will be made of benzenesulfonic acid and, as a preferred phosphonic acid, mention will be made of phenylphosphonic acid.

According to the invention, the $X^-$ anions derived from the acids HF, HCl, HBr, Hl, H$_2$SO$_4$ and H$_3$PO$_4$ are more particularly preferred.

Thus, anions $X^-$ which are particularly preferred according to the invention are the halide, sulfate, hydrogen sulfate, phosphate, hydrogen phosphate and dihydrogen phosphate anions. Tetrafluoroborates and hexaphenyl phosphates may also be mentioned as anions.

The bases which can be used for the deprotonation of the salts of formula VIII.1 are strong bases chosen from alkali metal hydrides, alkali metal hydroxides, alkali metal carboxylates, alkali metal alkoxides and alkali metal amides.

Examples of a suitable base are therefore sodium hydride, potassium hydroxide, sodium methoxide, potassium tert-butoxide, lithium diisopropylamide and mixtures thereof.

The deprotonation reaction is preferably carried out in a solvent capable of dissolving the starting salt of formula VIII.1, and also the other reagents.

Generally, the reaction temperature is between 40° C. and −78° C., preferably between 30 and −50° C., better still between 25 and −40° C., for example between 20 and −30° C.

Solvents which can be used in the method for preparing the carbenes are cyclic or noncyclic ethers, such as diethyl ether, diisopropyl ether, tetrahydrofuran, dioxane, dimethoxyethane or diethylene glycol dimethyl ether. Other solvents which can be used are dimethyl sulfoxide, dimethylformamide, dimethylacetamide, hexamethylphosphorylamide: [(CH$_3$)$_2$N]$_3$PO and hexamethylphosphoramide [(CH$_3$)$_2$N]$_3$P.

The carbenes of formula II in which A and B both represent a carbon atom can also be prepared by reduction of the corresponding thiones of formula IX:

$$\begin{array}{c} T_4\diagdown A \diagup N^{T_1} \\ \phantom{T_4}\|\phantom{A}\diagdown C=S \\ T_3\diagup B \diagdown N \diagup \\ \phantom{T_3}\phantom{B}T_2 \end{array} \xrightarrow[\Delta]{K} \begin{array}{c} T_4\diagdown A \diagup N^{T_1} \\ \phantom{T_4}\|\phantom{A}\diagdown C: \\ T_3\diagup B \diagdown N \diagup \\ \phantom{T_3}\phantom{B}T_2 \end{array}$$

IX

This reaction was described by N. Kuhn in Synthesis, 1993, 561. Preferably, the reduction is carried out in a solvent of the ether or amide type, as defined above, at a temperature of between 50 and 150° C., in the presence of potassium.

As regards the starting salts of formula (VIII.1), they can be prepared by reaction of the corresponding imidazoles, pyrazoles, triazoles and tetrazoles with an appropriate acid.

The nature of the anion $X^-$ in the salts of formula (VIII.1) depends on the acid used in this step. The acids which can be used are, for example, those which are listed above and from which $X^-$ derives.

Another method for synthesizing the salts of formula (VIII.1) in which A=B=C is described in U.S. Pat. No. 5,077,414.

This method comprises reacting an α-dicarbonyl compound (X) of formula:

$$T_4-\underset{\underset{O}{\|}}{C}-\underset{\underset{O}{\|}}{C}-T_3 \qquad X$$

in which $T_3$ and $T_4$ are as defined above, with HCHO and two amines of formulae $T_1$—NH$_2$ and $T_2$—NH$_2$ in the presence of an appropriate acid.

Other methods for preparing the salts of formula (VIII.1) are provided in Chem. Eur. J. 1996, 2, No. 12, pages 1627–1636 and Angew. Chem. Int. Ed. Engl. 1997, 36, 2162–2187.

The compounds of formula (IX) can be prepared by condensation of an appropriate thiourea of formula (XI):

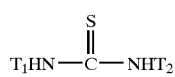

with an α-hydroxy ketone of formula (XII):

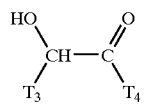

in which $T_1$, $T_2$, $T_3$ and $T_4$ are as defined above. Suitable operating conditions are in particular described by N. Kuhn in Synthesis, 1993, 561.

According to a particularly preferred embodiment of the invention, the metal complex of the invention has the formula:

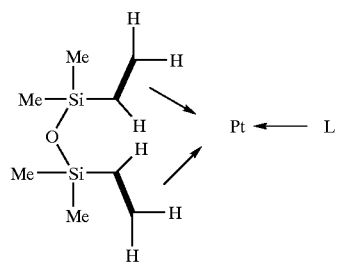

in which L is as defined above.

A simple method for preparing this complex consists in reacting the carbene L with the Karstedt catalyst of mean formula $Pt_2[ViMe_2Si\text{—}O\text{—}SiMe_2Vi]_3$ in which Vi represents the vinyl radical.

This reaction can be carried out with or without a solvent.

Examples of suitable solvents are cyclic or noncyclic ethers, such as diethyl ether, diisopropyl ether, tetrahydrofuran, dioxane, dimethoxyethane or diethylene glycol dimethyl ether; amides such as dimethylformamide or dimethylacetamide; and aromatic hydrocarbons (such as toluene, xylenes and more particularly toluene).

Advantageously, the reaction is carried out in an ether, and preferably in tetrahydrofuran.

The reaction temperature conventionally ranges between 10 and 50° C., preferably between 15 and 35° C., very preferably between 20 and 25° C.

It is preferable to work in the presence of a slight excess of carbene relative to the platinum. Thus, the molar ratio of the carbene L to the platinum generally ranges between 1 and 1.3, preferably between 1 and 1.1.

A simple way in which to carry out the procedure consists in pouring a solution of carbene, at the appropriate temperature, into a solvent, in a reactor containing a solution of the Karstedt catalyst in this same solvent.

The molarity of the solutions of carbene and of catalyst is not critical according to the invention.

The synthons contain at least one hydrocarbon ring in which is included an oxygen atom, and have the formula:

(1)

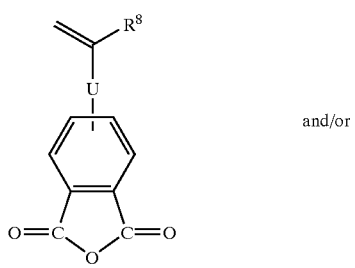

in which:
(i) the symbols Z, which may be identical or different, correspond to a divalent hydrocarbon radical chosen from the linear or branched alkylene radicals containing from 1 to 12 carbon atoms, one of the symbols Z possibly being a free valency;
(ii) the symbol U corresponds to a free valency or a divalent radical chosen from the linear or branched alkylene radicals containing from 1 to 12 carbon atoms and possibly containing a hetero atom, preferably an oxygen atom;
(iii) the symbol $R^8$ corresponds to a hydrogen atom or monovalent hydrocarbon radical chosen from the linear or branched alkyl radicals containing from 1 to 12 carbon atoms, and preferably a hydrogen atom or a methyl radical;

(2)

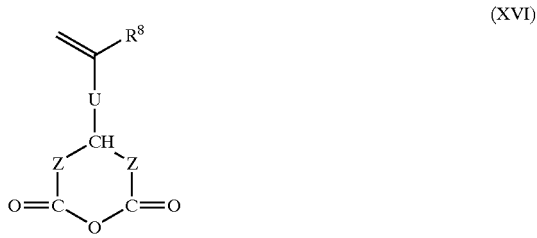

in which:
(i) the symbols Z, which may be identical or different, correspond to a divalent hydrocarbon radical chosen from the linear or branched alkylene radicals containing from 1 to 12 carbon atoms, one of the symbols Z possibly being a free valency;
(ii) the symbol U corresponds to a free valency or a divalent radical chosen from the linear or branched alkylene radicals containing from 1 to 12 carbon atoms and possibly containing a hetero atom, preferably an oxygen atom;

(iii) the symbol $R^8$ corresponds to a hydrogen atom or monovalent hydrocarbon radical chosen from the linear or branched alkyl radicals containing from 1 to 12 carbon atoms, and preferably a hydrogen atom or a methyl radical;

and (3)

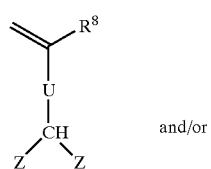

(XVII)

and/or

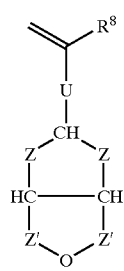

(XVIII)

in which:

(i) the symbols Z, which may be identical or different, correspond to a divalent hydrocarbon radical chosen from the linear or branched alkylene radicals containing from 1 to 12 carbon atoms and possibly containing at least one hydroxyl function; one of the symbols Z possibly being a free valency for (XVII) and the two symbols Z can be simultaneously a free valency for (XVIII);

(ii) the symbols Z', which may be identical or different, correspond to a divalent hydrocarbon radical chosen from the linear or branched alkylene radicals containing from 1 to 12 carbon atoms; at least one of the symbols Z' possibly being a free valency;

(iii) the symbol U corresponds to a free valency or a divalent radical chosen from the linear or branched alkylene radicals containing from 1 to 12 carbon atoms, and possibly containing a hetero atom, preferably an oxygen atom;

(iv) the symbol $R^8$ corresponds to a hydrogen atom or monovalent hydrocarbon radical chosen from the linear or branched alkyl radicals containing from 1 to 12 carbon atoms, and preferably a hydrogen atom or a methyl radical.

Preferably, the hydrocarbon ring in which is included the hydrogen atom contains at most 8 atoms in said ring. In addition, the best results are obtained in accordance with the hydrosilylation method of the invention with synthons containing only one hydrocarbon ring in which is included an oxygen atom. In particular, the synthons used which give good results (see examples below) have the formula:

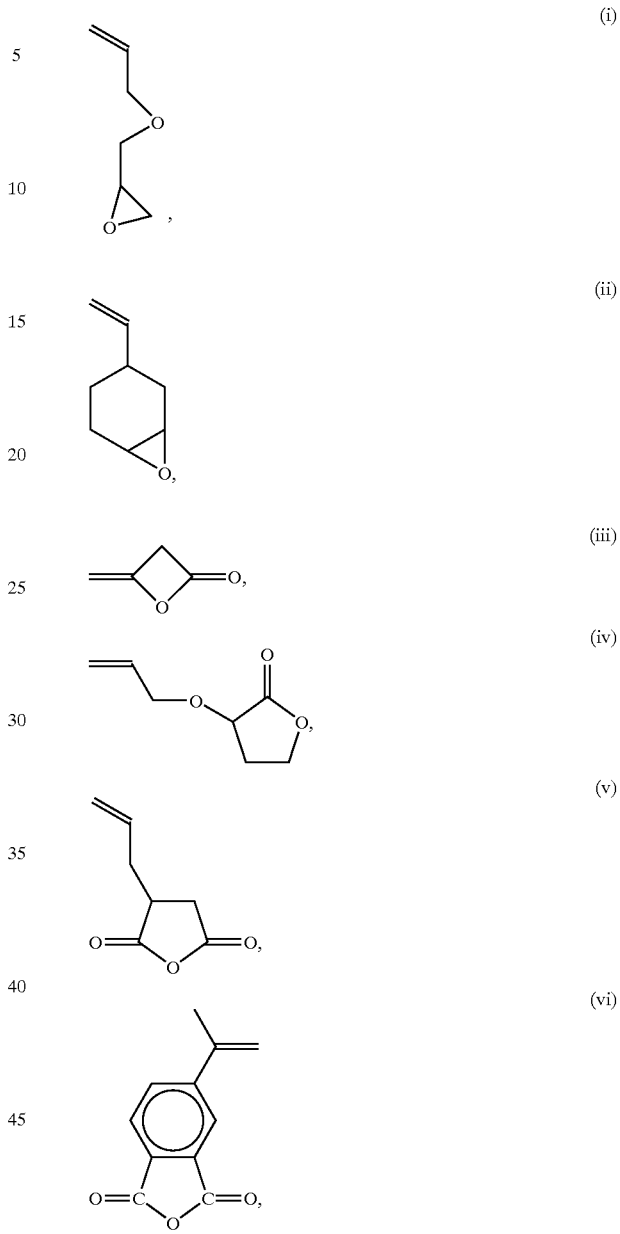

In general, the synthons which react with the polyorganohydrosiloxane are identical synthons. The polyorganohydrosiloxane/synthons molar ratio is between 0.01 and 100, preferably between 0.1 and 10.

The polyorganohydrosiloxanes used in the methods according to the invention are very diverse in nature. These polyorganohydrosiloxanes may be linear or cyclic and have the mean formulae:

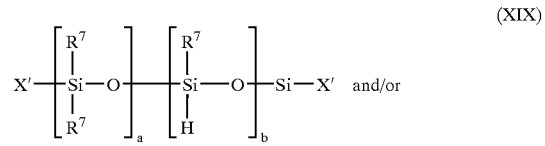

(XIX)

-continued

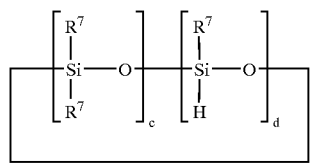
(XX)

in which:
the symbols R⁷ are identical or different and correspond to a monovalent hydrocarbon radical chosen from the phenyl radical and the linear or branched alkyl radicals containing from 1 to 6 carbon atoms, preferably 1 to 3 carbon atoms;
the symbols X' are identical or different and correspond to a monovalent radical chosen from R⁷, a hydrogen atom, a methoxy radical and an ethoxy radical;
a and b are integers or fractions, such that:
0<a≦200, preferably 0<a≦99
0≦b≦200, preferably 1<b≦100, and at least one of the two Xs corresponding to the hydrogen radical if b=0;
5<a+b≦200, preferably 10<a+b≦100
c and d are integers or fractions, such that
0<c<5, preferably 0<c<3
1<d<10, preferably 1<d<5,
3<a+b<10, preferably 3<a+b<5

The method according to the invention can be implemented according to various variants. By way of example, it is possible to use a first implementation in which all of the reagents and the catalytic composition are mixed in the reaction medium (batch type).

In the context of its experimental trials, the Applicant has developed an advantageous method in accordance with the first implementation. This method of hydrosilylation between a polyorganohydrosiloxane and an unsaturated synthon comprises the following steps:

(a) an amount of 5 to 5 000 ppm, preferably of 10 to 100 ppm, of catalytic metal complex relative to the total mass of the reagents is introduced, under inert gas, into the reaction medium;

(b) the synthon is introduced into the reaction medium;

(c) said medium is heated to a temperature of between 25° C. and 200° C., and preferably between 50° C. and 160° C;

(d) the polyorganohydrosiloxane is then introduced over a period of between 0 and 24 hours, preferably between 2.5 and 5 hours, the synthon/silicone molar ratio being between 1 and 1.10;

(e) the functionalized silicone oil is finally devolatalized.

This advantageous method can be carried out in bulk, which means that the reaction between the polyorganohydrosiloxane and the synthon takes place in the absence of solvent. However, many solvents, such as toluene, xylene, octamethyltetrasiloxane, cyclohexane or hexane, can be used.

The heterocycles of the oils obtained are virtually unpolymerized after hydrosilylation.

It should be noted that the oils prepared in accordance with the methods according to the invention exhibit lower levels of coloration and of turbidity than those prepared from the same raw materials using a catalyst of the Karstedt type. In particular cases, the oils obtained according to the invention are non-turbid and/or colorless. In the context of our invention, the expression "zero coloration" is intended to mean a coloration of less than 90 hazen, and preferably less than 40 hazen. As regards the turbidity, the oils are non-turbid when their turbidity is less than 1 NTU and/or they now exhibit only minimal traces of turbidity.

The measured epoxy content of the oils obtained according to the invention is very high and the measured epoxy content/theoretical epoxy content ratio is between 0.95 and 1, this theoretical epoxy content corresponding to the content of ≡SiH measured on the polyorganohydrosiloxane before reaction. This demonstrates that the method makes it possible to obtain a product with controlled viscosity (absence of phenomenon of gelling due to the epoxy functions).

The silicone oils according to the invention, because of their properties, are therefore used as an additive (for example as a diluent) or as a main component (for example as a resin) for the preparation of crosslinkable compositions used to prepare inks, varnishes and/or transparent and colorless coatings. In general, these crosslinkable compositions comprise a photoinitiator, a resin which is organic and/or silicone with epoxy and/or acrylate functionality; in addition, these compositions can comprise a diluent and/or a solvent. These compositions are crosslinkable, as appropriate, for example under UV radiation and/or under an electron beam.

EXAMPLES

The examples below illustrate the preparation of functionalized silicone oils obtained according to the method of the present invention.

1. Preparation of the Catalytic Metal Complex

The catalyst of formula (XXI) is prepared from the Karsted catalyst and a solution of carbene synthesized according to a procedure based on those described in the document "*Heterocyclic carbenes: a high yielding synthesis of novel, functionalized N-heterocyclic carbenes in liquid ammonia*", by W. A. Hermann et al., Chem. Eur. Journal, 1996, 2 page 1627.

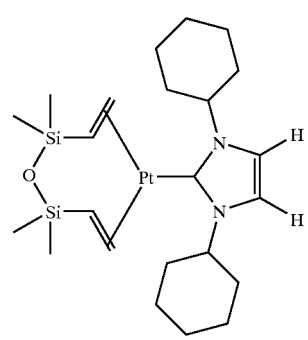
(XXI)

The epoxide functions are assayed by potentiometry. The device used is the Mettler brand, model DL21, equipped with a Mettler Toledo DG 113 SC LiCl/EtOH 1.0M combined electrode. The titrating solution is a solution of 0.1N perchloric acid in acetic acid.

The concentration of platinum is calculated relative to the total amount of the stoichiometric alkene +SiH oil mixture.

2. Preparation of Epoxidized Silicone Oil with Catalytic Complex (XXI)

21.48 g (173 mmol) of 4-vinylcyclohexene oxide (VCMX) are placed in a 100 ml reactor. The reaction mixture is heated to 70° C. with agitation. 20 µl (10 ppm) of a solution of the catalytic metal complex (XXI) at 2.68% for platinum in toluene are added to the reactor and 35 g (157.3 mmol) of heptamethylhydrotrisiloxane are then poured dropwise, over 3 hours, onto the VCMX.

After reaction for 5 hours, the degree of transformation of the SiH units is 99.5%, and 0.5% of the epoxide functions have disappeared. After reaction for 7 hours, the degree of transformation of the SiH units is 99.8%, and 1% of the epoxide functions have disappeared. The viscosity of the reaction crude at 25° C. is measured: v=6 mPa/s.

3. Counter Example: Preparation of Epoxidized Silicone Oil with Karsted Catalyst 21.48 g (173 mmol) of 4-vinylcyclohexene oxide (VCMX) are placed in a 100 ml reactor. The reaction mixture is heated at 70° C. with agitation. 5.5 μl (10 ppm) of a solution of Karstedt catalyst at 10% for platinum are added to the reactor and 35 g (157.3 mmol) of heptamethylhydrosiloxane are then poured dropwise, over 3 hours, onto the VCMX.

After reaction for 5 hours, the degree of transformation of the SiH units is 99%, but 12% of the epoxide functions have disappeared. After reaction for 7 hours, the degree of transformation of the SiH units is 99.3%, and 23% of the epoxide functions have disappeared. The viscosity of the reaction crude at 25° C. is measured: v=38 mPa/s.

The viscosity value for the oil of example 3 is 6 times higher than that of example 2, which means that some of the epoxide functions present in the medium have polymerized during the hydrosilylation reaction in the presence of the Karstedt catalyst.

4. Preparation of Epoxidized Silicone Oil with Catalytic Complex (XXI)

6.5 g (52.3 mmol) of 4-vinylcyclohexene oxide (VCMX) are placed in a 100 ml reactor. The reaction mixture is heated at 70° C. with agitation.

15.2 μl (10 ppm of Pt) of a solution of the catalytic metal complex (XXII) at 2.68% for platinum in toluene are added to the reactor and 45 g (47.6 mmol) of the polyhydrosiloxane of formula (XXII) given below are then poured dropwise, over 3 hours onto the VCMX.

$$Me_3SiO-(Me_2SiO)_{80}-(MeHSiO)_7-SiMe_3 \quad (XXII)$$

After reaction for 7 hours, the degree of transformation of the SiH units is 99.7%. The reaction is then stopped. After addition of 2.2 mg (60 ppm) of thiodiethanol, the reaction mixture is devolatilized under vacuum. The viscosity of the product after devolatilization is measured at 25° C.: v=325 mPa/s.

5. Counter Example: Preparation of Epoxidized Silicone Oil with Karstedt Catalyst 6.5 g (52.3 mmol) of 4-vinylcyclohexene oxide (VCMX) are placed in a 100 ml reactor. The reaction mixture is heated at 70° C. with agitation. 5.1 μl (10 ppm of Pt) of a solution of Karstedt catalyst at 10% for platinum are added to the reactor and 45 g (47.6 mmol) of the polyhydrosiloxane of formula (XXII) are then poured dropwise, over 3 hours, onto the VCMX.

After reaction for 5 hours, the degree of transformation of the SiH units is 99.9%. The reaction is then stopped. After addition of 2.2 mg (60 ppm) of thiodiethanol, the reaction mixture is devolatilized under vacuum. The viscosity of the product after devolatilization is measured at 25° C.: v=1700 mPa/s.

The viscosity value for the oil of example 5 is 5 to 6 times higher than that of example 4, which means that some of the epoxide functions present in the medium have polymerized during the synthesis in the presence of the Karstedt catalyst.

What is claimed is:

1. A method of carrying out a hydrosilylation reaction of synthons with at least one polyorganohydrosiloxane, comprising the step of: reacting the synthons, which are different or identical, and comprise at least one hydrocarbon ring in which is included an oxygen atom, with the polyorganosiloxane, in the presence of a catalytic metal complex of formula I:

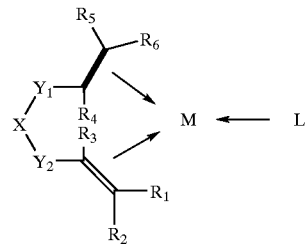

wherein:

M represents a metal in the 0 oxidation state chosen from the metals of group 8 of the Periodic Table as published in Handbook of Chemistry and Physics, 65th edition, 1984–1985;

X represents O, $NR_a$ or $CR_fR_g$;

$Y_1$ and $Y_2$, which are identical or different, represent $CR_bR_c$ or $SiR_dR_e$;

$R_1$, $R_2$, $R_5$ and $R_6$, which are identical or different, are a hydrogen atom, an alkyl group or an aryl group optionally substituted with alkyl;

$R_3$, $R_4$, $R_a$, $R_b$, $R_c$, which are identical or different, are a hydrogen atom; an alkyl group; an acyl group; an aryl group optionally substituted with an alkyl; a cycloalkyl optionally substituted with an alkyl; or an arylalkyl group in which the aryl component is optionally substituted with alkyl;

$R_d$ and $R_e$, which are identical or different, are an alkenyl group; an alkynyl group; an alkyl group; an alkoxy group; an acyl group; an aryl group optionally substituted with an alkyl; a cycloalkyl group optionally substituted with an alkyl; or an arylalkyl group in which the aryl component is optionally substituted with alkyl; or else when $Y_1$ and $Y_2$, which are identical or different, represent $SiR_dR_e$, two groups $R_d$ linked to two different silicon atoms together form:

a chain of formula:

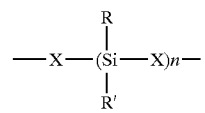

wherein n is an integer from 1 to 3; X is as defined above; R and R', which are identical or different, take any one of the meanings given above for $R_e$, with the proviso that, when n is 2 or 3, a single silicon atom of said chain is substituted with one or two alkenyl or alkynyl groups;

a saturated hydrocarbon chain, the two groups $R_d$ together with said silicon atoms and X forming a 6- to 10-membered ring; or else, when $Y_1$ and $Y_2$, which are identical or different, represent $CR_bR_c$, two groups $R_b$ linked to different carbon atoms together form a saturated hydrocarbon chain, the two groups $R_b$ together with the carbon atoms which bear them and X forming a 6- to 10-membered ring;

$R_f$ and $R_g$ represent, independently of one another, a hydrogen atom; an alkyl group; an acyl group; an aryl group optionally substituted with alkyl; a cycloalkyl group optionally substituted with alkyl; an arylalkyl group in which the aryl component is optionally substituted with an alkyl; a halogen atom; an alkenyl group; an alkynyl group; or a group $SiG_1G_2G_3$ wherein $G_1$, $G_2$ and $G_3$ are, independently of one another, an alkyl; an alkoxy; an aryl optionally substituted with an alkyl or an alkoxy; or an arylalkyl wherein the aryl component is optionally substituted with an alkyl or an alkoxy;

L represents a carbene of formula II:

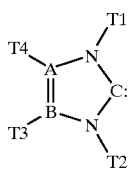

II wherein:

A and B, which are identical or different, represent C or N, with the proviso that, when A represents N, then $T_4$ represents nothing and when B represents N, then $T_3$ represents nothing;

$T_3$ and $T_4$, which are identical or different, represent a hydrogen atom; an alkyl group; a cycloalkyl group optionally substituted with an alkyl or an alkoxy; an aryl group optionally substituted with an alkyl or an alkoxy; an alkenyl group; an alkynyl group; or an arylalkyl group wherein the aryl component is optionally substituted with alkyl or alkoxy;

$T_1$ and $T_2$, which are identical or different, represent (i) an alkyl group; (ii) a perfluorinated alkyl group or an alkyl group optionally substituted with a perfluoroalkyl group; (iii) a cycloalkyl group optionally substituted with an alkyl or alkoxy group; (iv) an aryl group optionally substituted with an alkyl or alkoxy group; (v) an alkenyl group; (vi) an alkynyl group; or (vii) an arylalkyl group wherein the aryl component is optionally substituted with an alkyl or alkoxy group;

or else $T_1$ and $T_2$, which are identical or different, represent a monovalent radical of formula (V) below:

$$—V_1—V_2 \quad (V)$$

wherein:

$V_1$ is a divalent hydrocarbon radical, $V_2$ is a monovalent radical selected from the group consisting of:

alkoxy, $—OR^v$ with $R^v$ being hydrogen, alkyl, or aryl; and amine, or else alternatively, $T_1$ and $T_2$, independently represent a monovalent radical of formula (W) below:

$$—W_1\omega—W_2 \quad (W)$$

wherein:

$W_1$ is a divalent hydrocarbon radical,

ω represents:

$—R^\alpha C{=}CR^\alpha—$, with $R^\alpha$ being H, an alkyl group or $—C{\equiv}C—$ $W_2$ is a monovalent radical selected from the group consisting of:

$R^\beta$=alkyl, H;

Si-alkyl;

Si-alkoxy;

alcohol;

ketone;

carboxy;

amide; and acyl;

or else alternatively the substituents $T_1$, $T_2$, $T_3$ and $T_4$ form, in pairs, when they are located at two adjacent points in formula II, a saturated or unsaturated hydrocarbon chain.

2. The method as claimed in claim 1, wherein X represents O; $Y_1$ and $Y_2$ represent, independently of one another, $SiR_dR_e$.

3. The method as claimed in any one of the preceding claims, wherein $R_1$, $R_2$, $R_5$ and $R_6$ are hydrogen atoms.

4. The method as claimed in claim 1, wherein $R_3$ and $R_4$ is a hydrogen atom; an alkyl group; aryl optionally substituted with alkyl; or cycloalkyl optionally substituted with alkyl.

5. The method as claimed in claim 1, wherein A and B both represent a carbon atom.

6. The method as claimed in claim 1, wherein $T_3$ and $T_4$ represent a hydrogen atom.

7. The method as claimed in claim 1, wherein $T_1$ and $T_2$, which are identical or different, represent $(C_1-C_8)$alkyl or $(C_3-C_8)$cycloalkyl; or else $R_3$ and $R_4$, which are identical or different, represent $(C_1-C_8)$alkyl or $(C_3-C_8)$cycloalkyl; or else alternatively $T_1$, $T_2$, $R_3$ and $R_4$, which are identical or different, represent $(C_1-C_8)$alkyl or $(C_3-C_8)$cycloalkyl.

8. The method as claimed in claim 1, wherein M is a Pt, Pd and Ni.

9. The method as claimed in claim 1, wherein M is platinum in the 0 oxidation state.

10. The method as claimed in claim 1, wherein the metal complex has the formula:

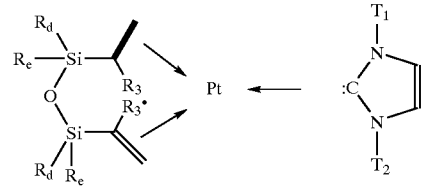

wherein:

$R_3$ represents a hydrogen atom; a $(C_1-C_8)$alkyl group; or a $(C_3-C_8)$cycloalkyl group optionally substituted with $(C_1-C_4)$alkyl; and $T_1$ and $T_2$ are identical and represent $(C_1-C_8)$alkyl or $(C_3-C_8)$cycloalkyl.

11. The method as claimed in claim 1, wherein the synthons contain a hydrocarbon ring in which is included an oxygen atom.

12. The method as claimed in claim 11, wherein the hydrocarbon ring in which is included an oxygen atom has the formula:

(1)

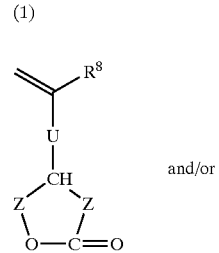

(XIII)

and/or

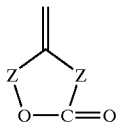
(XIV)

wherein:
(i) the symbols Z, which are identical or different, are divalent linear or branched alkylene radicals containing from 1 to 12 carbon atoms, optionally one of the symbols Z being a free valency;
(ii) the symbol U is a free valency or divalent linear or branched alkylene radicals containing from 1 to 12 carbon atoms optionnally containing a hetero atom;
(iii) the symbol $R^8$ is a hydrogen atom or a linear or branched alkyl radicals containing from 1 to 12 carbon atoms;

(2)

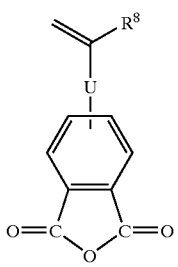
(XV)

and/or

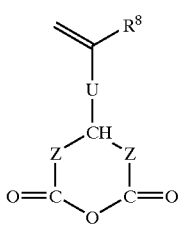
(XVI)

wherein:
(i) the symbols Z, which are identical or different, are divalent linear or branched alkylene radicals containing from 1 to 12 carbon atoms, optionally one of the symbols Z being a free valency;
(ii) the symbol U are a free valency or a divalent linear or branched alkylene radicals containing from 1 to 12 carbon atoms, optionally containing a hetero atom;
(iii) the symbol $R^8$ is a hydrogen atom or a linear or branched alkyl radicals containing from 1 to 12 carbon atoms; and (3)

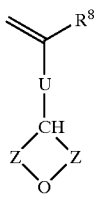
(XVII)

and/or

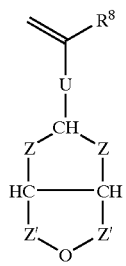
(XVIII)

wherein:
(i) the symbols Z, which are identical or different, are divalent linear or branched alkylene radicals containing from 1 to 12 carbon atoms optionally containing at least one hydroxyl function; one of the symbols Z being a free valency for (XVII) and the two symbols Z being simultaneously a free valency for (XVIII);
(ii) the symbols Z', which are identical or different, are divalent linear or branched alkylene radicals containing from 1 to 12 carbon atoms; at least one of the symbols Z' optionally being a free valency;
(iii) the symbol U is a free valency or a divalent linear or branched alkylene radicals containing from 1 to 12 carbon atoms, optionally containing a hetero atom;
(iv) the symbol $R^8$ are a hydrogen atom or monovalent hydrocarbon linear or branched alkyl radicals containing from 1 to 12 carbon atoms.

13. The method as claimed in claim 12, wherein the hydrocarbon ring of the synthons contains at most 8 atoms in said ring.

14. The method as claimed in claim 1, wherein the silicone oil is linear or cyclic and has the mean formulae:

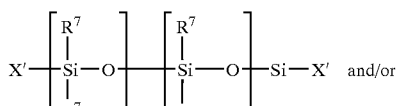
(XIX)

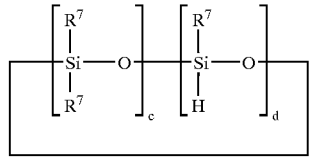
(XX)

wherein:
the symbols $R^7$ which are identical or different, are phenyl or linear or branched alkyl radicals containing from 1 to 6 carbon atoms;
the symbols X' which are identical or different, are a monovalent radical $R^7$, a hydrogen atom, a methoxy radical or an ethoxy radical;
a and b are integers or fractions, such that:
$0 < a \leq 200$,
$0 \leq b \leq 200$, and at least one of the two Xs corresponding to the hydrogen radical if b=0;
$5 < a+b \leq 200$, and
c and d are integers or fractions, such that:
$0 < c < 5$,
$1 < d < 10$, and
$3 < a+b < 10$.

* * * * *